United States Patent [19]
DeCamp et al.

[11] Patent Number: 5,442,056
[45] Date of Patent: Aug. 15, 1995

[54] PREPARATION OF 2-ARYL CARBAPENEMS

[75] Inventors: Ann E. DeCamp, Scotch Plains; Edward J. J. Grabowski, Westfield; Mark A. Huffman, Scotch Plains; Lyndon C. Xavier, Piscataway; Nobuyoshi Yasuda, Mountainside, all of N.J.

[73] Assignee: Merck & Co., Inc., Rahway, N.J.

[21] Appl. No.: 245,101

[22] Filed: May 17, 1994

[51] Int. Cl.$^6$ .................................. C07D 487/00
[52] U.S. Cl. ........................................ 540/302
[58] Field of Search ............................ 540/302

[56] References Cited

U.S. PATENT DOCUMENTS

| | | |
|---|---|---|
| 3,038,926 | 6/1962 | Farthouat . |
| 3,090,801 | 5/1963 | Washburn et al. . |
| 5,143,914 | 9/1992 | DiNinno et al. . |
| 5,153,186 | 10/1992 | DiNinno et al. . |
| 5,338,875 | 8/1994 | DeCamp et al. ............... 540/302 |

FOREIGN PATENT DOCUMENTS

0444889A1 of 0000 European Pat. Off. .

OTHER PUBLICATIONS

Chemistry Letters, pp. 1405–1408, 1989.
J. Am. Chem. Soc. 1985, 107, 972–980.
J. Med. Chem. 1987, 30, 871–880.
J. Org. Chem. 1990, 55, 5833–5847.
Synthetic Communications, 11(7), 513–519 (1981).
Synthetic Communications, 20(14), 2185–2189 (1990).
Tetrahedron Letters vol. 21, pp. 4221–4224, 1980.
Tetrahedron Letters vol. 29, No. 45, pp. 5739–5742, 1988.
Tetrahedron Letters vol. 29, No. 47, pp. 6043–6046, 1988.
Tetrahedron Letters vol. 31, No. 12, pp. 1665–1668, 1990.
Tetrahedron Letters vol. 31, No. 20, pp. 2853–2856, 1990.
Tetrahedron Letters vol. 31, No. 23, pp. 3291–3294, 1990.
Tetrahedron Letters vol. 31, No. 24, pp. 3389–3392, 1990.
Chemical Abstracts, vol. 106, No. 13, pp. 629–631 (1987).

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

The present invention is directed to a process of making 2-aryl carbapenems of formula 1 from a compound of formula A.

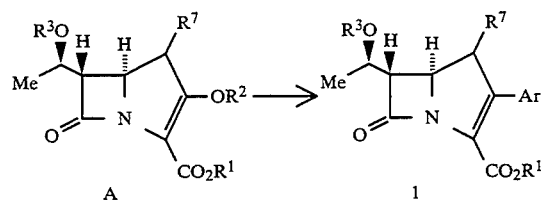

wherein compound A is reacted with a silyl protected boronic acid compound of the formula B:

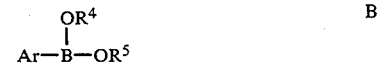

and wherein Ar is selected from the group consisting of:

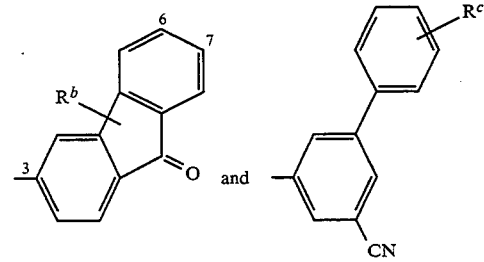

12 Claims, No Drawings

PREPARATION OF 2-ARYL CARBAPENEMS

BACKGROUND OF THE INVENTION

The invention disclosed herein concerns a process of making 2-aryl carbapenems. Carbapenem antibiotics, particularly thienamycin and imipenem (see U.S. Pat. Nos. 3,950,377 and 4,194,047) are two non-aryl substituted carbapenems which are well known for treating gram-negative and gram-positive bacterial infections. Active 2-aryl substituted carbapenems include those disclosed in U.S. Pat. Nos. 5,034,384 and 5,011,832.

As is generally appreciated, the carbapenem nucleus is unstable, thus necessitating mild coupling reagents. One alternative procedure utilizes stannane reagents which may introduce toxic impurities into the reaction medium, making purification of the product and subsequent processing difficult. See, e.g., Rano et al. *Tetrahedron Letters* 1990, 2853.

Related couplings with β-lactam containing substrates are given by Monroe and McDonald (Journal of Organic Chemistry 1989, 54, 5828), Kant (Tetrahedron Letters 1990, 3389), and Farina (Tetrahedron Letters 1988, 5739, 6043).

Boronic acid or ester couplings were reported by Snieckus (Tetrahedron Letters 1990, 1665), Suzuki (Chem. Letters 1989, 1405; Journal of the American Chemical Society 1985, 107, 972).

The boronic acid coupling methodology disclosed herein presents mild conditions, low toxicity and ease of product purification, such as those set forth in copending U.S. patent application No. 07/978,598 filed on Nov. 19, 1992. The present case contains unexpected improvements in the boronic acid-carbapenem reaction described therein.

Selected examples of the generalized palladium catalyzed coupling of organometallic agents with enol triflates are reported by Scott and McMurry (Accounts of Chemical Research, 1988, 21, 47), Stille (Angew. Chem International Edition English, 1986, 25, 508) and Piers (Tetrahedron Letters 1991, 4555).

SUMMARY OF THE INVENTION

The present invention is directed to a process of making 2-aryl carbapenems of formula 1.

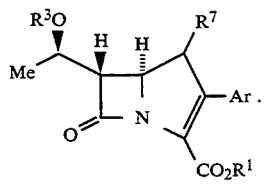

1

A compound of formula A:

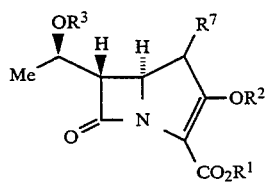

A wherein
—$OR^2$ is a leaving group selected from the group consisting of:

(a) triflate;
(b) fluorosulfonate;
(c) mesylate;
(d) tosylate and
(e) diaryl phosphate, wherein the aryl groups are unsubstituted or substituted phenyl and the substituents on each phenyl are independently 1–3 halo groups;

$R^1$ is a protecting group selected from the group consisting of:
(a) benzyl;
(b) p-methoxybenzyl,
(c) p-nitrobenzyl,
(d) o-nitrobenzyl,
(e) benzhydryl
(f) allyl,
(g) 2-trimethylsilylethyl and
(h) 2,2,2-trichloroethyl;

$R^3$ is selected from the group consisting of:
(a) hydrogen,
(b) a hydroxy protecting group selected from tri-$C_{1-4}$ alkyl silyl, phenyl di-$C_{1-4}$ alkyl silyl and diphenyl mono $C_{1-4}$ alkyl silyl;
(c) —$C(O)OR'^3$,
(d) $CH_2OR'^3$, and
(e) $R'^3$;

wherein $R'^3$ represents:
(a) benzyl,
(b) p-methoxybenzyl,
(c) p-nitrobenzyl,
(d) o-nitrobenzyl,
(e) benzhydryl
(f) allyl,
(g) 2-trimethylsilylethyl or
(h) 2,2,2-trichloroethyl;
and
$R^7$ is hydrogen or methyl;
is reacted with a silylated boronic acid compound of the formula B:

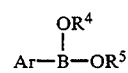

B wherein
Ar is selected from the group consisting of:

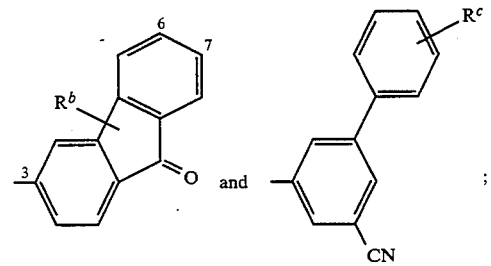

$R^b$ is selected from the group consisting of:
(a) $C_{1-3}$ alkyl,
(b) substituted $C_{1-3}$ alkyl, wherein the substituent is hydroxy, chloro, bromo, iodo or methoxy;
(c) hydroxy $C_{1-3}$ alkyl, wherein the hydroxy is protected with a silyl protecting group selected from tri-$C_{1-4}$ alkyl silyl, phenyl di-$C_{1-4}$ alkyl silyl and diphenyl mono $C_{1-4}$ alkyl silyl; and

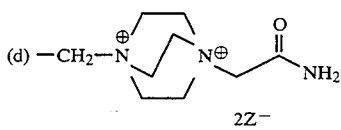

wherein $Z^-$ represents a negatively charged counterion;

$R^c$ is (a) $C_{1-3}$ alkyl,
(b) $C_{1-3}$ alkyl substituted with 1-3 groups selected from bromo, chloro and iodo;
(c) hydroxy $C_{1-3}$ alkyl, wherein the hydroxy is optionally protected with a silyl protecting group selected from tri-$C_{1-4}$ alkyl silyl, phenyl di-$C_{1-4}$ alkyl silyl and diphenyl mono $C_{1-4}$ alkyl silyl;

$R^4$ and $R^5$ are silyl protecting groups independently selected from: (a) tri-$C_{1-4}$ alkyl silyl; (b) phenyl di-$C_{1-4}$ alkyl silyl, and (c) diphenyl mono $C_{1-4}$ alkyl silyl, said phenyl groups being unsubstituted or independently substituted with 1-3 $C_{1-4}$ alkyl or halo groups, to produce a compound of formula 1.

DETAILED DESCRIPTION OF THE INVENTION

In one embodiment, the invention further concerns a process of making a 2-aryl carbapenem intermediate of formula 1, which comprises contacting a compound of Formula C:

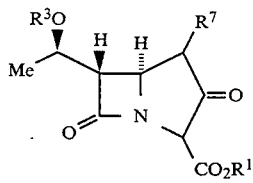

wherein $R^1$, $R^3$ and $R^7$ are as defined above, in a non-reactive solvent with an activating agent in the presence of a base to yield a compound of formula A;

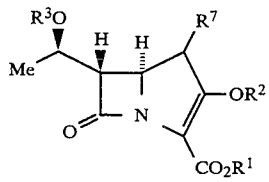

The group —$OR^2$ is a leaving group, such as
(a) triflate,
(b) fluorosulfonate,
(c) mesylate,
(d) tosylate,
(e) diaryl phosphate wherein the aryl group is mono or disubstituted phenyl and the substituents are each independently hydrogen or halo including chloro.

Compound A is reacted with the silylated boronic acid compound B in the presence of water, a base and a catalyst to produce the 2-aryl carbapenem intermediate of formula 1.

The molar ratio of Compounds A to B should be about 1 to 1.

The molar ratio of transition metal catalyst to compound B should be about 0.01 or greater; preferably about 0.01 to 0.10, e.g., about 0.03. The reaction is allowed to proceed until substantially complete, in about 1-24 hours (solvent dependent).

The 2-aryl carbapenem intermediate 1 can in many instances be reacted with neutral and quaternary ammonium side-chain forming intermediates to attach a side chain to the Ar moiety. In other cases, as illustrated below, a substituent can be attached to Ar before the silylated boronic acid coupling reaction is conducted. See, e.g., U.S. Pat. Nos. 5,034,384 and 5,011,832.

For purposes of this specification, the term "non-reactive solvents" includes halocarbon solvents, such as as mono or di-halo $C_{1-4}$ alkane including dichloromethane; ethereal solvents such as diethyl ether, t-butyl methyl ether, di-n-butyl and diisopropyl ethers, and cyclic ethers such as tetrahydropyran, and tetrahydrofuran; aromatic solvents such as benzene, toluene and xylene; and $C_{6-10}$ linear, branched or cyclic hydrocarbon solvent including hexane.

Halo includes Cl, Br, F and I.

"Activating agents" are defined to include bis-(3-chlorophenyl) chlorophosphate, diphenyl chlorophosphate, fluorosulfonic anhydride and trifluoromethanesulfonic anhydride, or others that will yield the substituent —$OR^2$.

The group —$OR^2$ in these instances, represents bis(chlorophenyl)phosphate, diphenylphosphate, fluorosulfonate, and trifluoromethane sulfonate, respectively.

Suitable bases include but are not limited to pyrrole, pyridine, pyrrolidine, imidazole and lutidine, di-$C_{1-3}$ alkylamine such as diisopropylamine and tri $C_{1-3}$ alkylamines such as triethylamine and diisopropyl ethylamine, metal amides, wherein metal is defined as sodium, potassium or lithium, including di-$C_{1-4}$ alkyl amides such as lithium diisopropylamide; $C_{1-4}$ alkyl metals such as n-butyllithium; metal $C_{1-4}$ alkoxides, such as potassium t-butoxide; metal hydrides such as sodium or potassium hydride; and metal carbonates, such as sodium and potassium carbonate.

The molar ratio of activating agent to compound C should be about 0.90 to 1.0. A ratio of 0.95 is typical.

The reaction may be conducted from about $-20°$ C. to $-80°$ C., preferably $-70°$ C. to $-80°$ C.

The reaction is allowed to proceed until substantially complete, in about 0.25-24 hours, typically about 0.25-6.0 hours.

The reaction is preferably conducted under nitrogen.

Another aspect of the present invention includes:

(B) contacting the compound of formula A' (wherein $R^3$ represents hydrogen), in a non-reactive solvent as defined above, with a protecting agent $R^3X$, suitable for removably protecting the hydroxyl group in the presence of a base to yield a compound of formula A in which $R^3$ represents a hydroxyl protecting group.

The protecting agent is $R^3X$ in which $R^3$ represents a protecting group and X represents a leaving group, e.g., halide, triflate and the like.

For purposes of this specification, the protecting groups ($R^3$) suitable for step (B) include triorgano silyl groups such as tri-$C_{1-3}$ alkyl silyl, including tri-methyl and tri-ethyl silyl and t-butyl di-methyl silyl. Also included is t-butyl di-phenylsilyl. Other suitable groups are found in Protective Groups in Organic Synthesis, Theodora W. Green, John Wiley and Sons (1981).

Preferred leaving groups (X) are defined to include chloro and triflate.

The molar ratio of compound A to the protecting agent R³X should be about 1 to 1, and preferably about 1:0.9.

The reaction should be allowed to proceed until complete, about 0.25 to 1.5 hours.

The reaction may be conducted at a temperature of from about −20° C. to about −80° C.

The reaction is preferably conducted under a nitrogen atmosphere.

Step (B) is preferably conducted in situ with the reaction mixture resulting from Step (A).

Alteratively, compound A can be isolated by standard means before continuing with the reaction scheme.

"Coupling bases" as used herein include but are not limited to metal hydroxides, such as barium, potassium, sodium, lithium and thallium; amine bases, such as hydroxyethylamine, trialkylamines, e.g., Et₃N, dialkylamines, e.g., diisopropylamine; aromatic amines, and metal carbonates such as potassium or sodium carbonate. The preferred base is a trialkylamine base, such as triethylamine.

"Coupling solvents" include di-$C_{1-3}$ alkyl formamides such as dimethyl formamide, di-$C_{1-3}$ alkyl sulfoxide such as dimethylsulfoxide, N-methylpyrrolidinone, N-ethylpyrrolidinone, as well as halocarbon solvents, such as mono or di-halo $C_{1-4}$ alkyl including dichloromethane; etheral solvents such as diethyl ether di-n-butyl and diisopropyl ethers, cyclic ethers such as tetrahydropyran, and tetrahydrofuran; aromatic solvents such as benzene, toluene and xylene; and $C_{6-10}$ linear, branched or cyclic hydrocarbon solvent including hexane.

Non-reactive solvents include halocarbon solvents such as mono or di-halo $C_{1-4}$ alkane including dichloromethane.

A standard phase transfer agent such as tetra-n-butylammonium salts and polyethyl-glycol reagents such as TWEEN 40 may be added to the reaction (about 0 to 5% of total volume).

"Transition metal catalysts" include Pd(0) catalysts, such as Pd (dba)₂, Pd₂(dba)₃, Pd₂(dba)₃·CHCl₃ wherein dba is defined as dibenzylideneacetone. As appreciated by those of skill in the art, other standard coordinating ligands may also be used. Pd$^{II}$ catalysts may also be employed including Pd(OAc)₂ and PdCl₂. Nickel catalysts are also included.

The compounds of Formula 1 which are the intermediates can then be converted to an active antibiotic compound by methods which are exemplified in U.S. Pat. Nos. 5,034,384 and 5,011,832. These patents are hereby incorporated by reference.

Another aspect of the invention encompasses intermediate compounds of formula B:

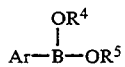

wherein Ar, R⁴ and R⁵ are as defined above.

In this aspect of the invention, the preferred Ar is fluoren-9-onyl. The structure shown herein contains a substituent group R$^b$ which is shown attached to a bond which is drawn in the center ring. This means that the R$^b$ group can be attached at any available point of attachment in either phenyl ring. The preferred point of attachment is at position 7.

Preferred Ar groups are also noted to include those wherein R$^b$ and R$^c$ represent —CH₂OH, protected forms of —CH₂OH, —OCH₃ and —CH₃. R$^b$ preferrably resides a position 7 of the fluorenone moiety as mentioned above, whereas R$^c$ is preferrably at position 4 of the biphenyl ring system.

Illustrative of the silylfluorenone boronic acids are the following species:

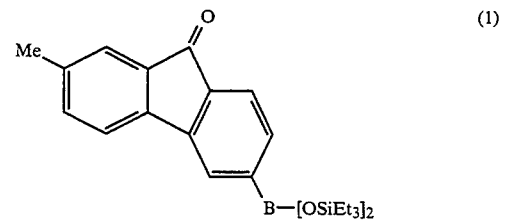

(1)

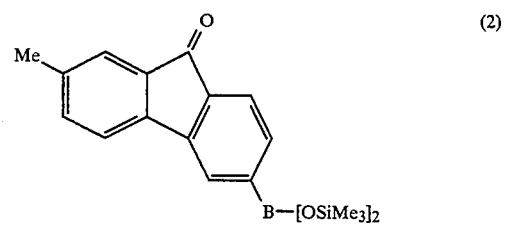

(2)

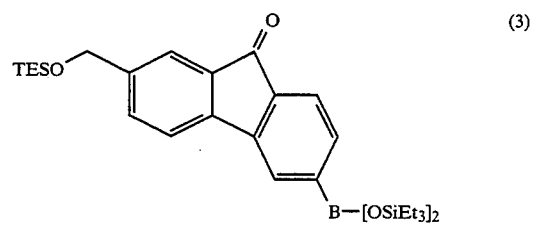

(3)

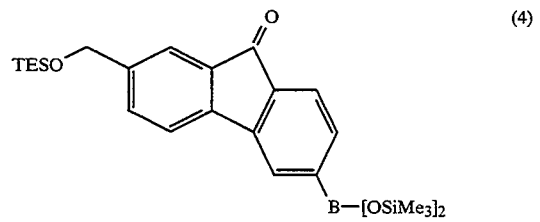

(4)

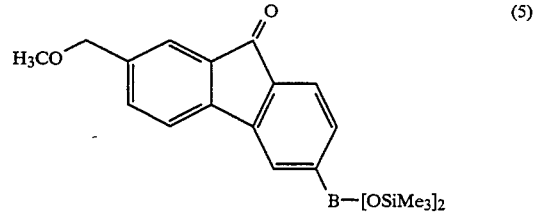

(5)

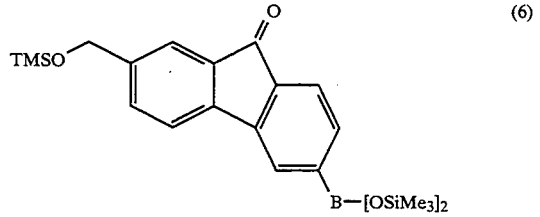

(6)

Me=Methyl
Et=Ethyl
TMS=trimethylsilyl
TBDMSO=t-butyldimethylsilyloxy
TESO=triethylsilyloxy The process can be practiced in accordance with the following reaction schemes and general description.

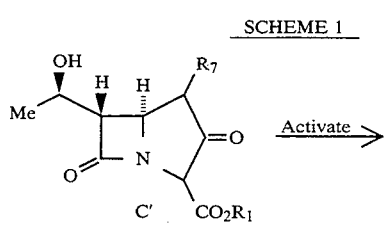

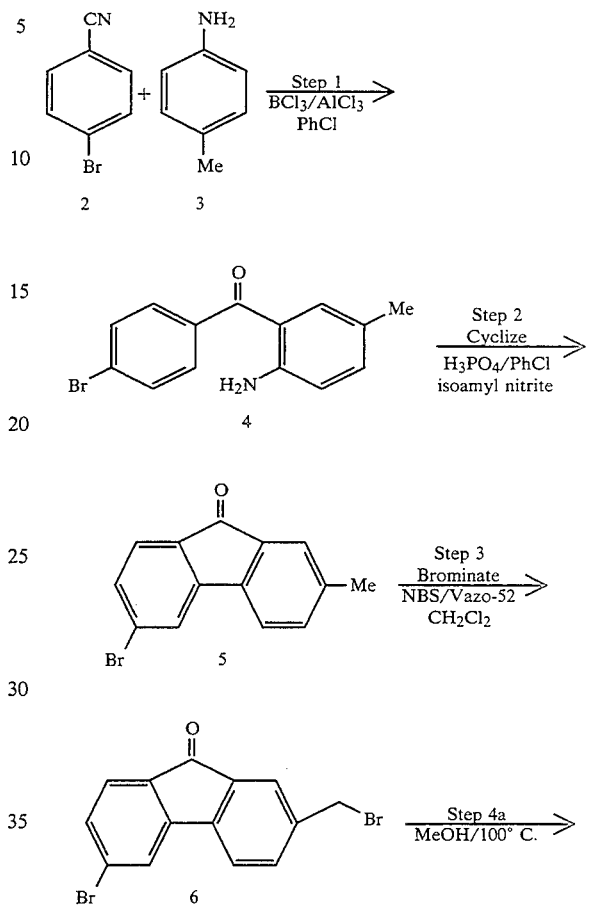

The silylated boronic acid compound B can be made in accordance with the following reaction scheme and description.

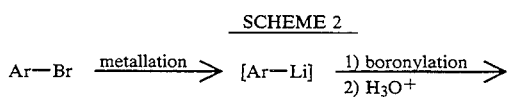

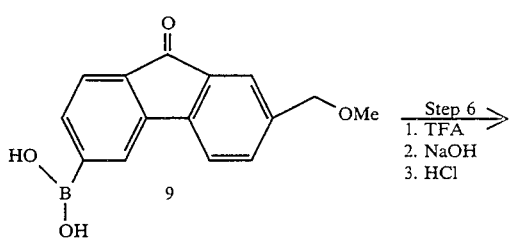

The aryl bromide, Ar—Br shown above in Scheme 2 undergoes metallation with, e.g., n-butyl lithium; is boronated with, e.g., B(O-i-propyl)$_3$; and is then acidified to form Ar—B(OH)$_2$. Further reaction with the silylating agent provides the intermediate silyl boronic acid compound B of the present invention.

The silylated fluorenone boronic acid moiety can be synthesized in accordance with U.S. Pat. No. 5,034,384, or alternatively, the process set forth below in Scheme 3 can be utilized.

-continued
SCHEME 3

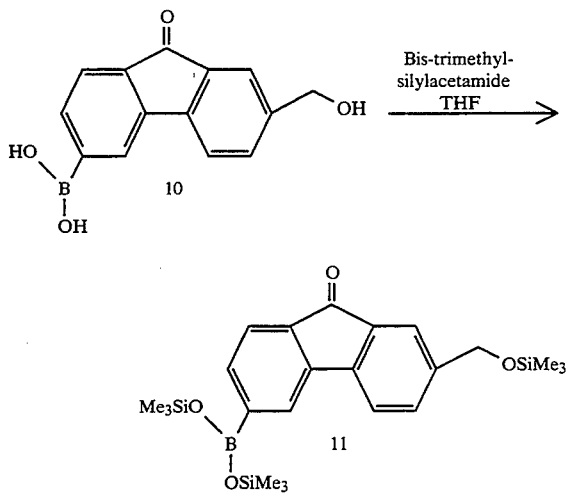

In this embodiment of the invention, p-bromobenzonitrile 2 and p-toluidine 3 undergo reaction in the presence of boron trichloride and aluminum trichloride to give the benzophenone derivative 4. In the cyclization step, the fluorenone ring is formed by diazotization of the aniline group with isoamyl nitrite, followed by ting closure to give 5. The benzylic position is brominated to give 6 with N-bromosuccinimide in the presence of an initiator, such as Vazo-52.

Prior to the attachment of the boronic acid group, the fluorenone carbonyl and the benzylic position are protected to give 8. Following this, the arylbromide 8 is metalated, in the presence of triisopropylborate, with n-BuLi to give after workup, the boronic acid 9. The benzylic methyl ether is cleaved with trifluoroacetic acid to give the hydroxymethylboronic acid intermediate 10. Bis(trimethylsilyl)acetamide or another silylating agent is used to silylate the boronic acid on all available hydroxy groups 11.

Surprisingly, appropriate selection of the silyl groups throughout the reaction scheme facilitates the formation of crystals upon coupling the aromatic side chain to the carbapenem nucleus.

As exemplified hereinunder, the group Ar may contain a carbonyl or other group that requires protection prior to further processing.

In another aspect of the invention, the fluorenone moiety can be substituted with a quaternary or bis quaternary group which is to be included in the final product. The appropriately substituted fluorenone silylboronic acid group can then be reacted with a compound of formula A. Illustrative of this aspect of the invention is Scheme 4.

SCHEME 4

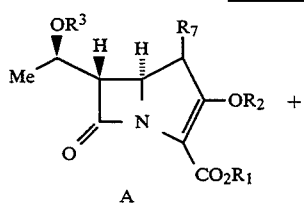

-continued
SCHEME 4

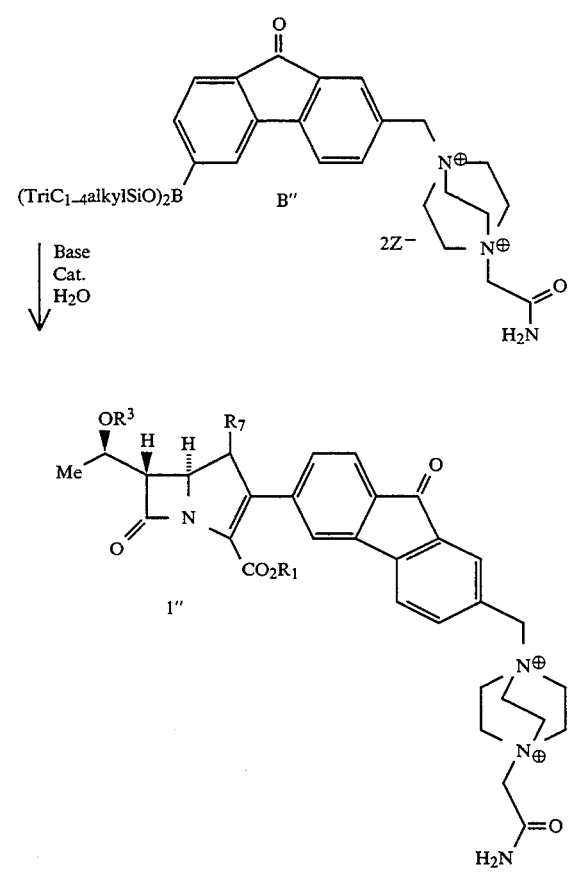

In this embodiment of the invention, the formation of Compound 1" is conducted in the presence of a coupling base, a Pd catalyst and water. Typically, protection of the acetamide nitrogen is unnecessary. The counterions $Z^-$ represent negatively charged species which are present in the system to provide overall charge balance. Such species can vary widely. For example, $Z^-$ may represent a sulfonate, such as a triflate or mesylate, or a halide anion, e.g., $Cl^-$, $Br^-$, $I^-$ and the like. A divalent anionic specie could alteratively be present, such as a sulfate dianion. The particular counterion or counterions which are present can be readily changed without departing from the invention.

The following examples illustrate the preparation of representative compounds of the invention, and as such, are not considered as limiting the invention. For further methods of preparing substituted fluorenonyl and biphenyl compounds, see U.S. Pat. Nos. 5,034,384 and 5,011,832.

PREPARATIVE EXAMPLE 1

Preparation of 2-Methoxymethylfluoren-9-on-6-ylboronic Acid by Solvolysis/Ketalization Protection Steps Followed by Metallation/Borylation

A. Solvolysis and Ketalization

6-Bromo-2-methoxymethyl-9-fluorenone Dimethyl Ketal

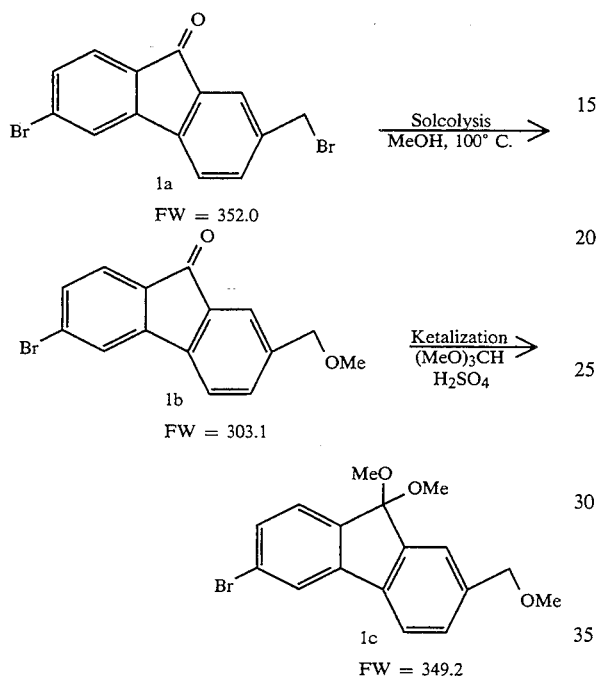

B. Metallation/Boronation

Preparation of 2-Methoxymethylfluoren-9-on-6-ylboronic Acid

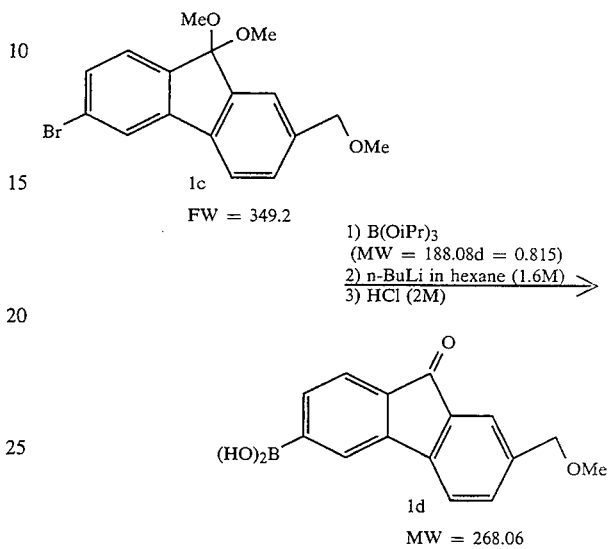

Part a—Conversion of Benzylic Bromide to Methyl Ether

Absolute methyl alcohol (200 mL; 10 mL/g) was charged to a dry glass-lined pressure-rated vessel equipped with a mechanical stirrer under a $N_2$ atmosphere. 6-Bromo-2-bromomethyl-9-fluorenone (20 g; 0.057 mol) was charged and the resulting slurry was heated at 100° C. in the sealed vessel for 24 hours. The mixture was cooled to room temperature. The methyl ether crystallized upon cooling.

Ketalization of the Carbonyl

The reaction mixture from Part a above was cooled to 0°–5° C. and sequentially charged with concentrated sulfuric acid (4.6 mL; and trimethyl orthoformate (93.5 mL, 0.855 mol). The reaction flask was fitted with a distillation head. The reaction mixture was heated and the distillate was collected (~60 mL) until the internal temperature reached 60° C. (still head temperature: 55° C.). The reaction mixture was then heated at 60° C. under reflux for 1.5 hours. The colorless to pale yellow solution was cooled to 10° C. Dry triethylamine (47.7 mL, 34.6 g, 0.34 mol; 4 mol/mol of $H_2SO_4$) was added to the stirred mixture. The solution was taken to a minimum volume (~57 mL) by distillation in vacuo (internal temperature <30° C.). The mixture was diluted with toluene (400 mL) and aqueous NaOH solution (400 mL, 1.0N) and agitated. The phases were separated and the aqueous phase was extracted with toluene (200 mL). The combined organic phases were washed twice with water (200 mL). The organic phase was filtered into the next reaction vessel and azeotropically dried by vacuum distillation of toluene. The solution was reduced to a minimum volume (57 mL) prior to the next reaction.

Into a dry three liter three necked round bottom flask equipped with a 500 mL addition funnel, thermocouple probe, and nitrogen inlet, were charged the solution of the ketal 1c in toluene (420 mL, 1.07M) and dry tetrahydrofuran (1.7 L) at room temperature. The air in the reaction flask was exchanged by three vacuum purges with nitrogen. Triisopropyl borate (150 mL, 651 mmol) was added to the solution at room temperature. The mixture was cooled to −78° C. and n-butyl lithium solution (1.6M in hexanes; 395 mL; 628 mmol) was slowly added over 3 hours, maintaining the temperature at −80° to −75° C.

After 30 minutes, an aliquot of the reaction mixture was taken for HPLC assay. Typically, 2.0 area % of the bromo compound remained. Additional n-butyl lithium solution (1.6M; 19 mL; 30.4 mmol) was added to the reaction mixture over 10 minutes at −80° to −75° C.

After aging for 20 minutes, a reaction aliquot was assayed by HPLC. In a typical case, 0.1 area % of the bromo compound remained. The reaction mixture was allowed to warmed to 20° C. over 1 hour. To the solution was added aqueous sulfuric acid (2M; 920 mL; 1.84 mol) over 10 minutes. The mixture was vigorously stirred for 30 minutes. The organic layer (2.62 L) was separated. The aqueous layer (1.2 L) was extracted with ethyl acetate (0.5 L and 0.2 L). The combined organic extracts were concentrated to 300 mL under 165 mm bar (38° C. bath). The product crystallized out. To this mixture was added water (450 mL), and the resulting three phase mixture was stirred overnight at room temperature. The precipitates were collected on a 600 mL sintered glass filtered, washed with toluene (100 mL) and water (3×150 mL), and dried under house vacuum (nitrogen sweep) at 80° C. overnight. 2-Methoxymethylfluoren-9-one-6-boronic acid 1d was obtained as a mono-hydrate (125.8 g, 91.1 wt % purity).

PREPARATIVE EXAMPLE 2

5-cyano-4'-hydroxyoxymethylbiphenyl-3-boronic Acid

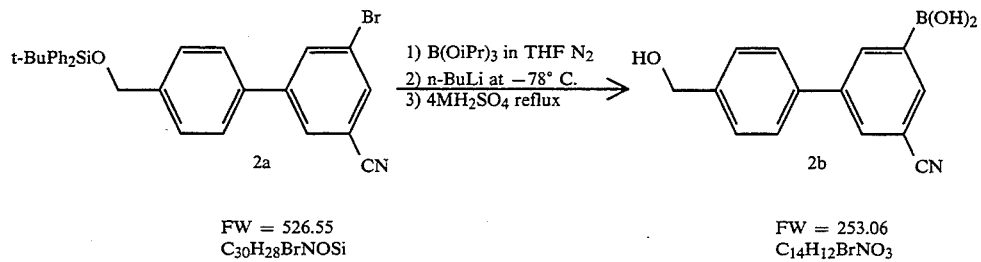

FW = 526.55
C30H28BrNOSi

FW = 253.06
C14H12BrNO3

To 1-bromo-4-tert-butyldiphenylsilyloxy-methylbenzene (1.224 Kg; 2.32 mol) was added dry THF (10.5 L) and B(OiPr)3 (794 mL; 3.44 mol; 1.48 eq) at room temperature under nitrogen. The air in the reaction flask was completely exchanged by three vacuum purges with nitrogen. The solution was cooled down to −78° C. To the solution was added 1.6M solution of n-BuLi in hexanes (2.08 L; 3.32 mol; 1.43 eq) at −78° to −75° C. over 2 hours. The mixture was allowed to warm up to 17° C. To the mixture was added 4M $H_2SO_4$ (4.64 L) at 5° C.

After cooling down to room temperature, 5M aqueous potassium hydroxide (7.7 L) was dropwise added to the mixture below 20° C. (pH was about 10.8). During neutralization, inorganic salt ($K_2SO_4$) was precipitated. To this mixture was added 1M aqueous potassium hydroxide (2.23 L) below 20° C. (pH was about 12.5). To this mixture was added t-butylmethyl ether (5 L) and stirred at room temperature for 30 minutes. The aqueous layer was separated and THF (2.5 L) was added to the aqueous solution. The aqueous solution was adjusted to pH 2.7 with conc. HCl below 20° C. The mixture was extracted after stirring with ethyl acetate (5 L), dried over $MgSO_4$, and concentrated in vacuo. The residual solid was dissolved in DMF (2.3 L) at 100° C. and added water (6.9 L) at 100° C. The mixture was cooled down to room temperature gently and aged at ambient temperature overnight. The crystals were collected by filtration, washed with 30% cold aqueous DMF (2 L), and then water (2 L), and dried at room temperature overnight to give 524 g of the desired biphenyl boronic acid 2b.

EXAMPLE 1

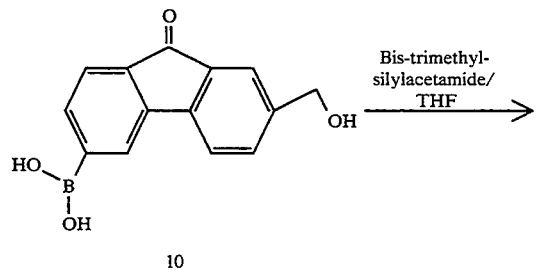

10

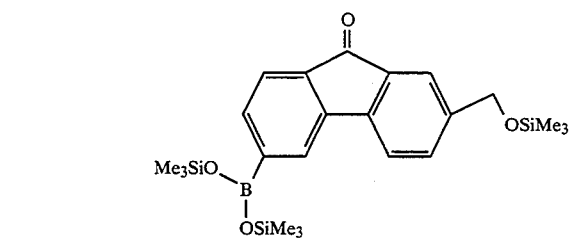

11

Bis(trimethylsilyl)acetamide (BSA) (FW 203.43, 1.804 l, 1.485 kg.) is dissolved in THF, heated to 30° C. and combined with 7-hydroxymethylfluoren-9-on-3-yl boronic acid 10 (FW 272.05, 993.18 g, 3.91 Mol) in a 22 L round bottom flask fitted with a steam bath and nitrogen line. This addition is conducted stepwise, maintaining the internal temperature between 35° C. and 45° C. The batch is stirred at 35° C. for 30 min., then cooled to about 0° C. to produce the tris(trimethyl)silylated fluorenone boronic acid 11.

EXAMPLE 2

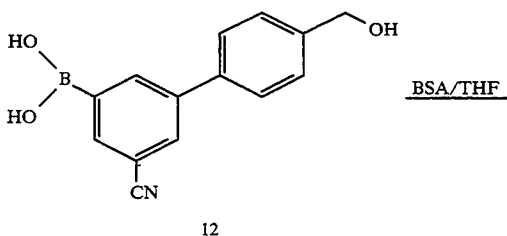

12

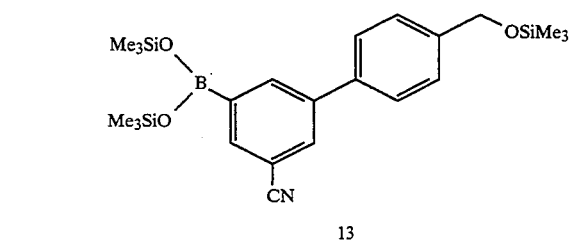

13

The cyanobiphenyl boronic acid 12 (FW 253.06, 1.0 eq.) is dissolved in THF at 20°-25 ° C. BSA (1.5 eq.) is added, and the solution is warmed to 35°-40° C. to produce the tris(trimethylsilylated) biphenyl 13.

EXAMPLE 3

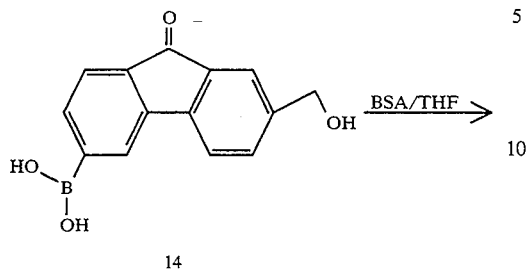

The boronic acid substituted fluorenone 14 (238 g/mole, 1.45 g, 6.08 mmol) is suspended in dry THF (25 ml). BSA (FW 203.43, 0.823 g/ml, 1.85 g (2.25 mL) 9.12 mmol) is added and the resulting solution is stirred for 1.25 hrs.

An additional 10.75 mL of BSA is added, and the solution is stirred until the reaction is complete, forming the bis-silylated fluorenone boronic acid 15.

EXAMPLE 4

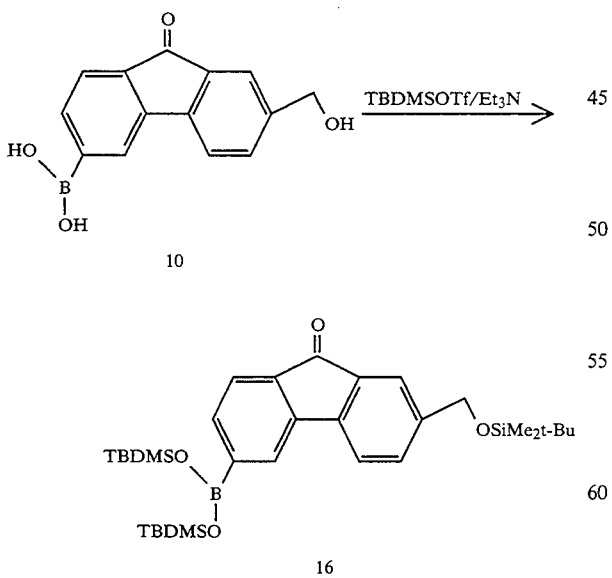

Substitute t-butyldimethylsilyl triflate and triethylamine into the reaction of Example 1 in place of BSA to produce the tris-TBDMS fluorenone boronic acid 16.

EXAMPLE 5

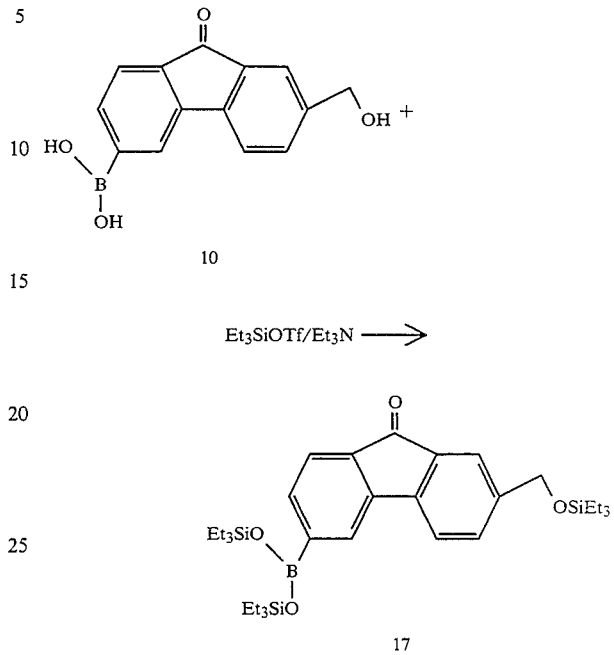

Substitute bis(triethylsilyl) triflate and triethylamine into the reaction of Example 1 to produce the tris(triethylsilyl)fluorenone boronic acid 17.

EXAMPLE 6

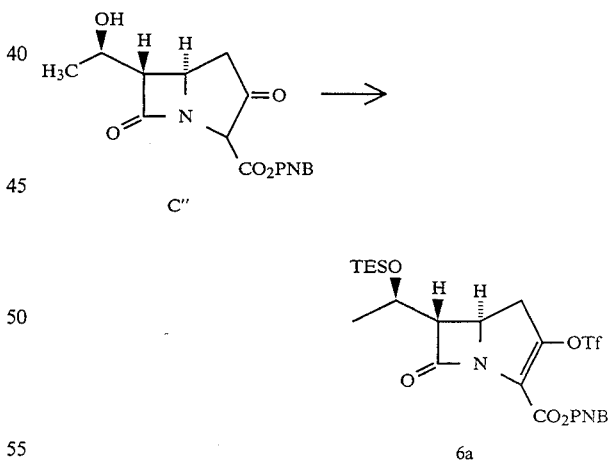

A. Preparation of 6a

Compound C" (1.4 g, 1.0 eq.) is added to THF (16 mL) at room temperature and cooled to −78° C. Triethylamine (TEA) (0.466 mg, 4.4 mMol, 1.1 eq.) and triflic anhydride (Tf2O)(4.4 mMol, 1.242 mg, 0.74 mL, 1.1 eq) are added. TEA (1.1 eq) and triethylsilyl triflate (TESOTf) (4.4 mMol., 1.1 eq.) are added stepwise at −78° C. to produce Compound 6a

B. Preparation of 11

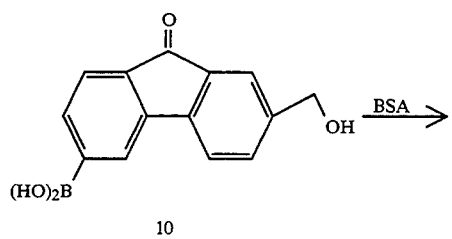

Compound 10 (272.05 g/mole, 4.0 mMol) is reacted in accordance with the procedures of Example 1 to produce Compound 11.

C. Formation of Compound 6c

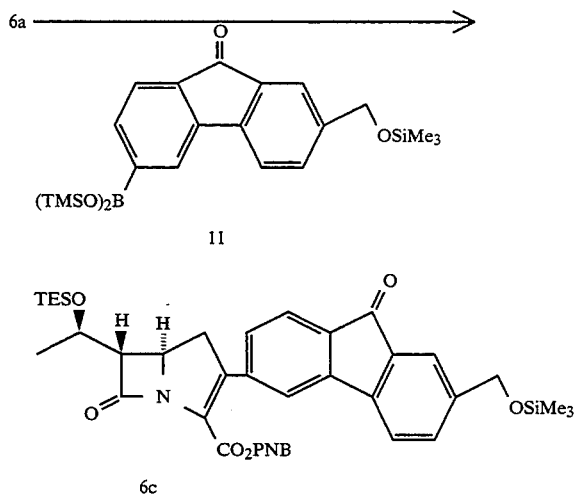

The solutions from part A and B are combined at −78° C. Pd(dba)₂ (84 mg.) is added, followed by KOH (2.2 mL, 3.0 eq., 5.4N) and toluene (16 mL). The reaction is stirred at room temperature to completion.

The reaction mixture is washed with citric acid (5%, 100 mL). The aqueous fraction is back-extracted with toluene and the organic layers are combined and dried over MgSO₄, filtered and dried to give 1.18 g of Compound 6c.

EXAMPLE 7

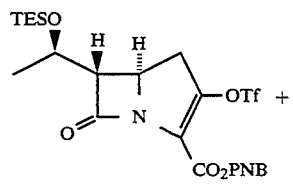

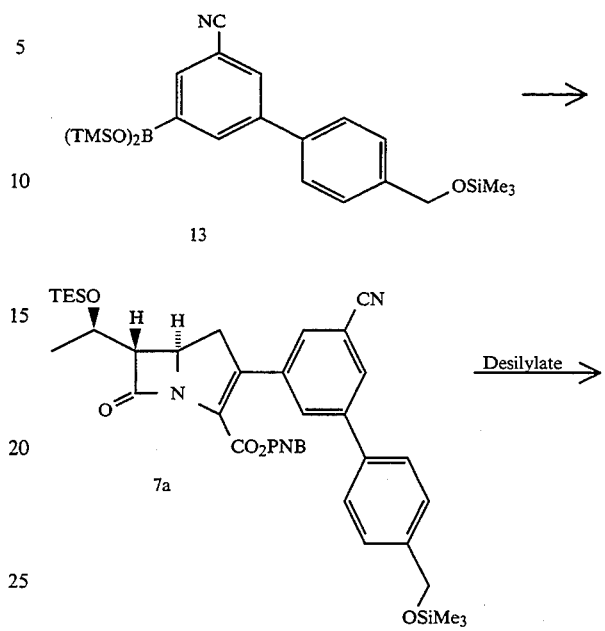

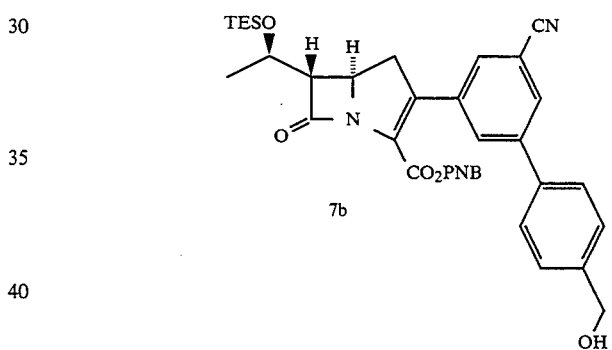

Preparation of Compounds 6a and 13

Compound 6a is prepared as described in Example 6A, and Compound 13 is prepared in accordance with Example 2.

Formation of Compound 7a

A solution of Compound 6a (0.24 mMol) in CH₂Cl₂ (1.2 mL) kept at −78° C. is combined with a solution of compound 13 (1.0 eq. generated in situ) in THF. The temperature is allowed to rise to −60° C., and Pd(dba)₂ (11.85 mg), THF (1.2 mL), KOH (5.4N, 165 μL, 0.889 mMol, 3.75 eq) are added. The reaction is allowed to stand at room temperature to completion (4 hrs) to produce Compound 7a.

The TMS group of Compound 7a is removed in THF under aqueous acid conditions to produce Compound 7b.

EXAMPLE 8

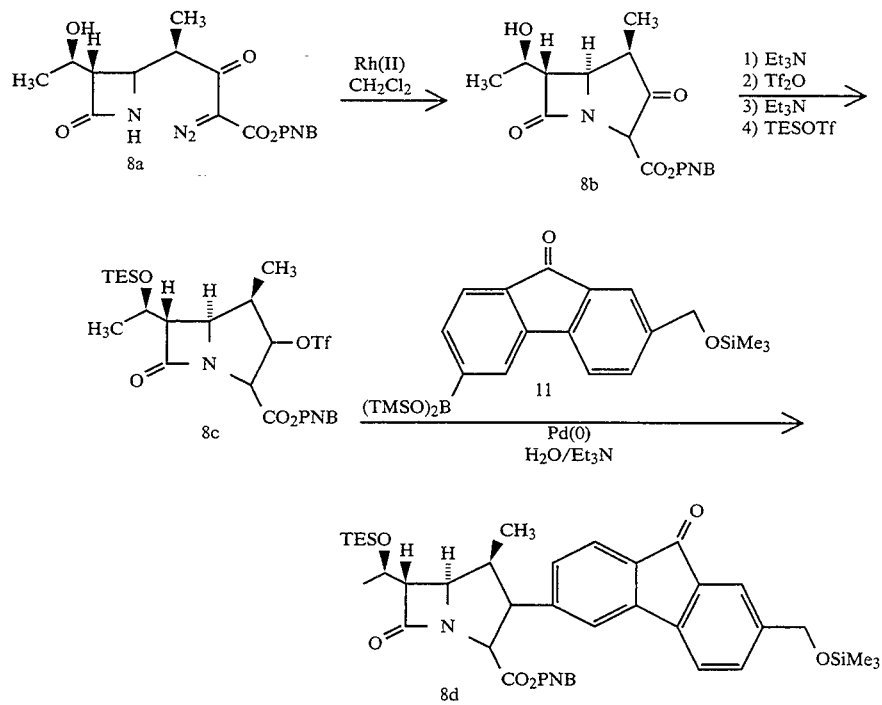

A 50 L round bottom flask is fined with a stirrer, steam bath, reflux condenser and nitrogen line. The flask is flushed with nitrogen and charged with ZnBr$_2$ (FW 225.19, 8.65 g, 38.42 mMol), Rh (II) octanoate (FW 778.63, 14.958 g, 19.21 mMol) and CH$_2$Cl$_2$ (15.0 L). Compound 8a (FW 390.4, 1500.0 g, 3.84 Mol) is added. The flask is sparged with N$_2$ and heated to reflux for 3.0 hrs, producing compound 8b.

The solution of compound 8b is cooled to −78° C. with dry ice/acetone. Triethylamine (FW 101.19, 535 mL, 3.84 Mol), triflic anhydride (FW 282.13, 646 mL, 3.84 Mol), Et$_3$N (669 mL, 4.8 Mol) and triethylsilyl triflate (FW 264.34, 956 mL, 4.2 Mol) are sequentially added via an addition funnel, maintaining the batch temperature below −70° C. to produce compound 8c.

Compound 11 is prepared in accordance with Example 1.

The CH$_2$Cl$_2$ solution of compound 8c is treated with a final portion of Et$_3$N (1,017 mL, 7.3 Mol) and the THF solution of compound 11 is added. The combined solution is sparged with N$_2$. Water (138.473 mL) and Pd(0)(dba)$_2$ (FW 575.00, 66 g, 115 mMol) are added and the solution is warmed to 30° C.

After completion (2–3 hrs.), the solution is cooled, transferred to a 100 L cylindrical vessel, diluted with hexanes (9 L) and extracted (2×) with aqueous NaCl (23%, 44 L each). The solution is filtered through Solka Floc, rinsing with CH$_2$Cl$_2$/hexanes (1:1).

The solvent is switched to CH$_3$OH by vacuum distillation, and crystal formation is noted. After completely switching to CH$_3$OH, the slurry is filtered and rinsed with CH$_3$OH. The product, Compound 8d, is dried under vacuum with N$_2$ sweep, yielding 1982 g.

EXAMPLE 8A

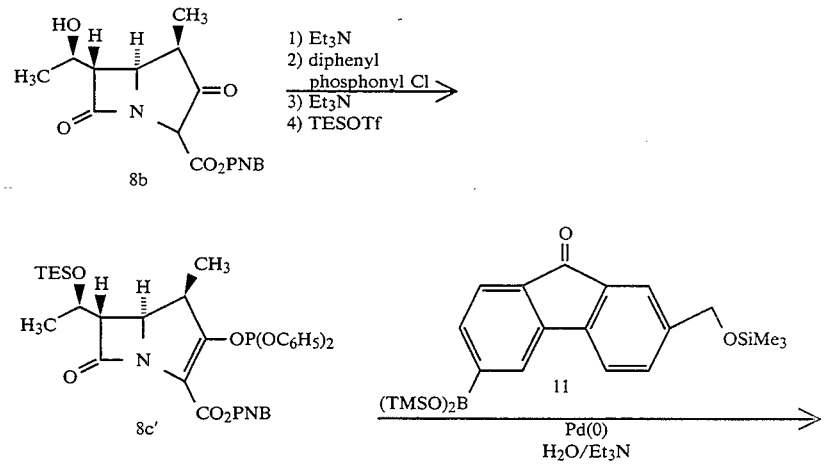

-continued

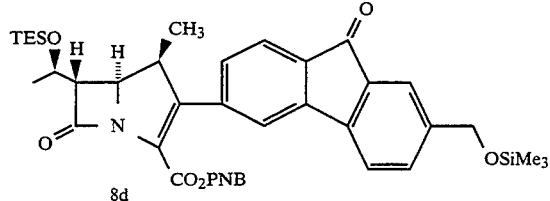
8d

Substitute diphenyl phosphonyl chloride for triflic anhydride in the procedure set forth in Example 8 to produce the diphenyl phosphonyl compound 8c'.

EXAMPLE 9

Desilylation Reaction

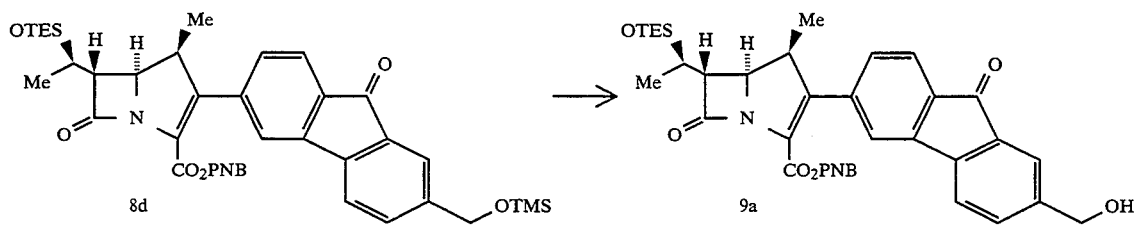

Procedure

To a 100 L cylindrical flask, equiped with a nitrogen inlet and a thermocouple, was added tetrahydrofuran (50 L). To the flask was added Compound 8d (3.45 Kg) with a rinse of THF (5.2 L). To this solution was added a solution of phthalic acid potassium acid salt (0.05M; 22.08 L, pH 4.0). Initially, this mixture was two phases, but during the reaction the mixture became homogeneous. The reaction was monitored by HPLC.

After stirring at room temperature for 16 hours, the starting material was typically at a 0.5 area % level. To the solution was added solid NaCl (5.52 Kg). The mixture became two-phases. The aqueous layer was separated. The THF layer was washed with sat. NaHCO$_3$ solution (22 L), then sat. NaCl solution (22 L). The THF solution was concentrated in vacuo to approximately 4 L.

The residue was diluted with t-BuOMe (50 L) and washed with 2.5 wt % NaCl solution (22 L). The organic layer was concentrated to approximately 20 L and flushed with 20 L of t-BuOMe twice to give 20 L of solution. The t-BuOMe solution was slowly added to a stirred mixture of heptane (60 L) which contained seed crystals. The mixture was aged overnight with stirring. The product was collected by filtration, washed with heptane (10 L), and dried under vaccum to give the product, Compound 9a (2.90 Kg).

EXAMPLE 10

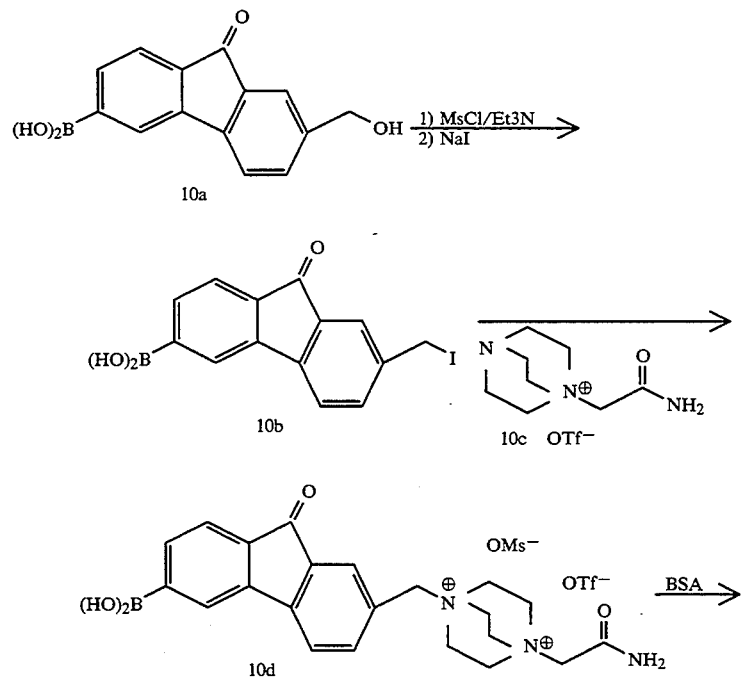

-continued

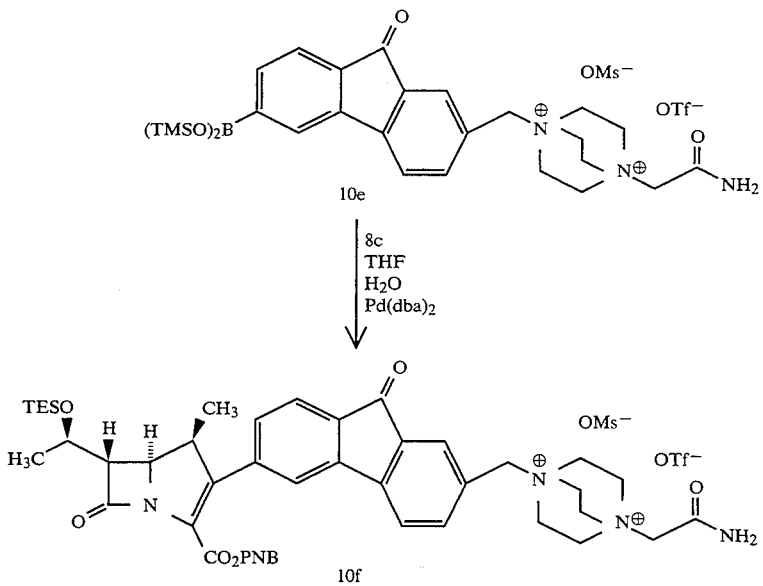

Compound 10a may be activated with mesyl chloride in the presence of Et$_3$N and then reacted with sodium iodide in THF to produce compound 10b.

The cationic side chain is attached by reacting compound 10b with 1-(aminocarbonylmethyl)-4-aza-1-azoniabicyclo(2.2.2)octane trifluoromethanesulfonate 10c in THF at 0°–50° C. producing the bisquaternary compound 10d.

Compound 10d is silylated with BSA according to the procedures set forth in Examples 1, 2 and 6B, thus producing the silylated boronic acid compound 10e.

Compounds 8c and 10e are coupled in THF, H$_2$O and Et$_3$N in the presence of Pd(dba)$_2$ to produce the bisquaternary carbapenem 10f.

What is claimed is:

1. A process of making a 2-aryl carbapenem of the formula 1:

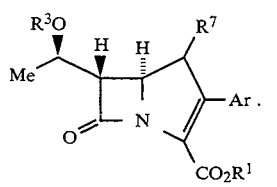

comprising reacting a compound of formula A:

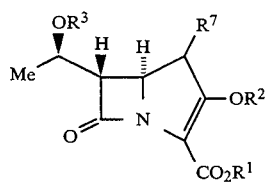

in which

—OR$_2$ is a leaving group selected from the group consisting of:
   (a) triflate;
   (b) fluorosulfonate;
   (c) mesylate;
   (d) rosylate and
   (e) diaryl phosphate, wherein the aryl groups are unsubstituted or substituted phenyl and the substituents on each phenyl are independently 1-3 halo groups;

R$^1$ is a protecting group selected from the group consisting of:
   (a) benzyl;
   (b) p-methoxybenzyl,
   (c) p-nitrobenzyl,
   (d) o-nitrobenzyl,
   (e) benzhydryl
   (f) allyl,
   (g) 2-trimethylsilylethyl and
   (h) 2,2,2-trichloroethyl;

R$^3$ is selected from the group consisting of:
   (a) hydrogen,
   (b) a hydroxy protecting group selected from tri-C$_{1-4}$ alkyl silyl, phenyl di C$_{1-4}$ alkyl silyl and diphenyl mono C$_{1-4}$ alkyl silyl;
   (c) —C(O)OR$'^3$,
   (d) CH$_2$OR$'^3$, and
   (e) R$'^3$;

wherein R$'^3$ represents:
   (a) benzyl,
   (b) p-methoxybenzyl,
   (c) p-nitrobenzyl,
   (d) o-nitrobenzyl,
   (e) benzhydryl
   (f) allyl,
   (g) 2-trimethylsilylethyl or
   (h) 2,2,2-trichloroethyl;
and R$^7$ is hydrogen or methyl;

with a silylated boronic acid compound of the formula B:

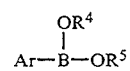

in which Ar is selected from the group consisting of:

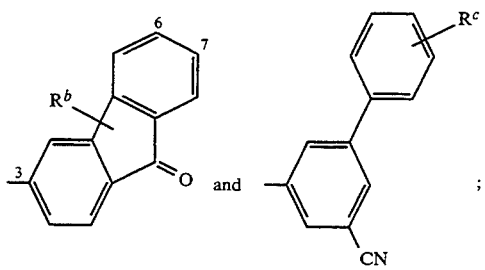

$R^b$ is selected from the group consisting of:
(a) $C_{1-3}$ alkyl,
(b) substituted $C_{1-3}$ alkyl, wherein the substituent is hydroxy, chloro, bromo, iodo or methoxy;
(c) hydroxy $C_{1-3}$ alkyl, wherein the hydroxy is protected with a silyl protecting group selected from tri-$C_{1-4}$ alkyl silyl, phenyl di $C_{1-4}$ alkyl silyl
(d) and diphenyl mono $C_{1-4}$ alkyl silyl; and

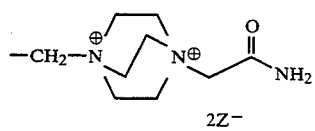

wherein $Z^-$ represents a negatively charged counterion;
$R^c$ is selected from the group consisting of:
(a) $C_{1-3}$ alkyl,
(b) $C_{1-3}$ alkyl substituted with 1–3 groups selected from bromo, chloro and iodo;
(c) hydroxy $C_{1-3}$ alkyl, wherein the hydroxy is optionally protected with a silyl protecting group selected from tri-$C_{1-4}$ alkyl silyl, phenyl di $C_{1-4}$ alkyl silyl and diphenyl mono $C_{1-4}$ alkyl silyl;
$R^4$ and $R^5$ are silyl protecting groups independently selected from: (a) tri-$C_{1-4}$ alkyl silyl; (b) phenyl di $C_{1-4}$ alkyl silyl, and (c) diphenyl mono $C_{1-4}$ alkyl silyl, said phenyl groups being unsubstituted or independently substituted with 1–3 $C_{1-4}$ alkyl or halo groups,
to produce a compound of formula 1.

2. A process in accordance with claim 1 wherein compound A is reacted with compound B in the presence of a coupling base, a coupling solvent and a catalyst.

3. A process according to claim 2 wherein the catalyst is a palladium or nickel catalyst.

4. A process in accordance with claim 2 wherein the catalyst is Pd(dibenzylideneacetone)$_2$.

5. A process according to claim 1 further comprising: contacting the compound of formula A':

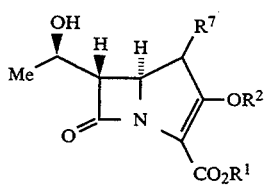

with a protecting agent $R^3X$ suitable for removably protecting a hydroxyl group in the presence of a nitrogen containing base, wherein $R^3$ represents a protecting group and X represents a leaving group, to yield a compound of formula A:

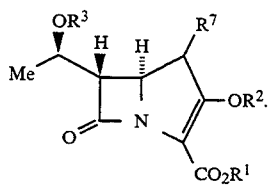

6. A process according to claim 2 wherein the solvent is dichloromethane.

7. A process according to claim 5 wherein the protecting agent $R^3X$ is triethylsilyl trifluoromethane sulfonate.

8. A process of making a 2-aryl carbapenem of the formula 1:

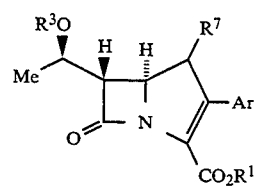

comprising:
(A) contacting a compound of formula C':

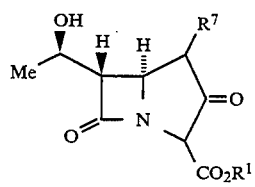

wherein $R^1$ is selected from the group consisting of:
(a) benzyl;
(b) p-methoxybenzyl,
(c) p-nitrobenzyl,
(d) o-nitrobenzyl,
(e) benzhydryl
(f) allyl,
(g) 2-trimethylsilylethyl and
(h) 2,2,2-trichloroethyl;
and $R^7$ is hydrogen or methyl;
with an activating agent in the presence of a base to yield a compound of formula A';

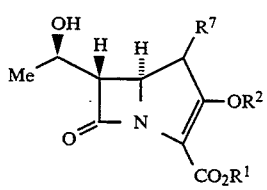

wherein
—$OR^2$ is a leaving group selected from the group consisting of:
(a) triflate,
(b) fluorosulfonate,
(c) mesylate,
(d) tosylate and (e) diaryl phosphate wherein the aryl group is phenyl unsubstituted or substituted with from 1–3 halo groups;

(B) contacting the compound of formula A' with a protecting agent $R^3X$ suitable for removably protecting the hydroxyl of Formula A' in the presence of a nitrogen containing base to yield a compound of formula A:

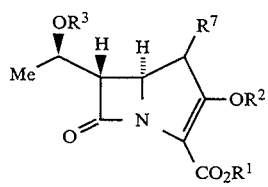

in which $R^3$ represents a protecting group and a leaving group X;

(C) contacting the compound of formula A and a coupling base and water in a coupling solvent in the presence of a palladium catalyst with a compound of the formula B:

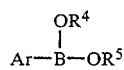

in which Ar is selected from the group consisting of:

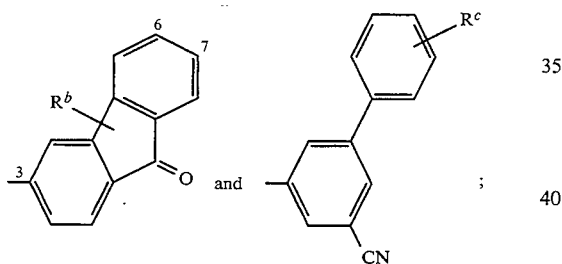

$R^b$ is selected from the group consisting of:
(a) $C_{1-3}$ alkyl,
(b) substituted $C_{1-3}$ alkyl, wherein the substituent is hydroxy, chloro, bromo, iodo or methoxy;
(c) hydroxy $C_{1-3}$ alkyl, wherein the hydroxy is protected with a silyl protecting group selected from tri-$C_{1-4}$ alkyl silyl, phenyl di $C_{1-4}$ alkyl silyl
(d) and diphenyl mono $C_{1-4}$ alkyl silyl; and

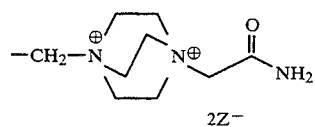

wherein $Z^-$ represents a negatively charged counterion;
$R^c$ is selected from the group consisting of:
(a) $C_{1-3}$ alkyl,
(b) $C_{1-3}$ alkyl substituted with 1–3 groups selected from bromo, chloro and iodo;
(c) hydroxy $C_{1-3}$ alkyl, wherein the hydroxy is optionally protected with a silyl protecting group selected frown tri-$C_{1-4}$ alkyl silyl, phenyl di $C_{1-4}$ alkyl silyl and diphenyl mono $C_{1-4}$ alkyl silyl;

$R^4$ and $R^5$ are silyl protecting groups independently selected from: (a) tri-$C_{1-4}$ alkyl silyl; (b) phenyl di $C_{1-4}$ alkyl silyl, and (c) diphenyl mono $C_{1-4}$ alkyl silyl, said phenyl groups being unsubstituted or independently substituted with 1–3 $C_{1-4}$ alkyl or halo groups, to produce a compound of Formula 1.

9. A process according to claim 8 wherein the palladium catalyst is Pd(dibenzylideneacetone)$_2$.

10. A process according to claim 8 wherein the coupling solvent is dichloromethane.

11. A process according to claim 8 wherein the protecting agent $R^3X$ is triethylsilyl trifluoromethane sulfonate.

12. A process in accordance with claim 8 wherein:
$R^1$ is p-nitrobenzyl;
$R^3$ is triethylsilyl;
$R^7$ is β-methyl;
Ar is

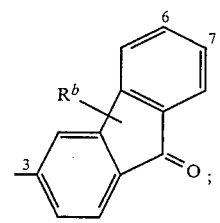

in which $R^b$ is as previously defined and is attached at position 7, comprising:

(A) contacting a compound of formula C':

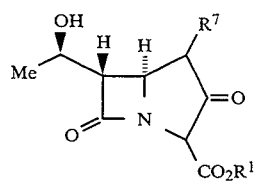

in a non-reactive solvent with an activating agent in the presence of a base to yield a compound of formula A';

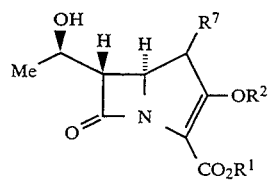

(B) contacting the compound of formula A' in a nonreactive solvent with a protecting agent $R^3X$ suitable for removably protecting the hydroxyl of formula A' in the presence of a nitrogen containing base to yield a compound of formula A:

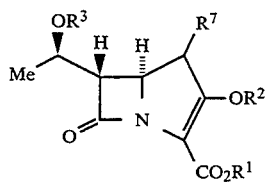 A
wherein R³ represents a protecting agent and X is a leaving group;
(C) contacting the compound of formula A and a coupling base in a coupling solvent with a compound of the formula B:
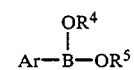 B
and a palladium catalyst to yield a compound of Formula 1.
* * * * *